(12) United States Patent
Mosimann et al.

(10) Patent No.: US 8,104,774 B2
(45) Date of Patent: Jan. 31, 2012

(54) HAND-HELD INSTRUMENT FOR DENTAL OR SURGICAL USE

(75) Inventors: David Mosimann, Bienne (CH); Vincent Mosimann, legal representative, La Neuveville (CH); Luc Maître, Epauvilliers (CH)

(73) Assignee: Bien-Air Holding SA, Bienne (CH)

( * ) Notice: Subject to any disclaimer, the term of this patent is extended or adjusted under 35 U.S.C. 154(b) by 254 days.

(21) Appl. No.: 12/089,219

(22) PCT Filed: Jan. 23, 2007

(86) PCT No.: PCT/EP2007/050621
§ 371 (c)(1),
(2), (4) Date: Apr. 4, 2008

(87) PCT Pub. No.: WO2007/124962
PCT Pub. Date: Nov. 8, 2007

(65) Prior Publication Data
US 2008/0299514 A1 Dec. 4, 2008

(30) Foreign Application Priority Data
May 3, 2006 (EP) .................................... 06113410

(51) Int. Cl.
*B25G 3/02* (2006.01)
(52) U.S. Cl. ............................ 279/51; 433/127; 433/129
(58) Field of Classification Search .......... 433/126–129, 433/114, 130–134; 606/79–80, 167, 170; 279/43, 51–53, 30, 74–76, 82, 905
See application file for complete search history.

(56) References Cited

U.S. PATENT DOCUMENTS

| | | | | | |
|---|---|---|---|---|---|
| 261,795 | A | * | 7/1882 | Weber | 433/129 |
| 2,341,529 | A | * | 2/1944 | Cohen | 279/52 |
| 3,475,817 | A | * | 11/1969 | Loge | 433/129 |
| 3,994,070 | A | * | 11/1976 | Loge | 433/127 |
| 4,802,852 | A | * | 2/1989 | Shea | 433/127 |
| 5,055,044 | A | * | 10/1991 | Kuhn | 433/126 |
| 5,478,093 | A | | 12/1995 | Eibl et al. | |
| 2006/0234184 | A1 | * | 10/2006 | Grimm | 433/114 |

FOREIGN PATENT DOCUMENTS

| | | |
|---|---|---|
| DE | 44 21 658 A1 | 1/1995 |
| FR | 2 248 014 A1 | 5/1975 |
| FR | 2 342 052 A1 | 9/1977 |
| WO | 2005/089666 A1 | 9/2005 |
| WO | WO 2005/089666 A1 * | 9/2005 |

OTHER PUBLICATIONS 5 pages of machine translation of WO 2005/089666 A1.*

* cited by examiner

*Primary Examiner* — Cris L Rodriguez
*Assistant Examiner* — Edward Moran
(74) *Attorney, Agent, or Firm* — Young & Thompson

(57) ABSTRACT

A hand-held instrument, for dental or surgical use, intended to rotate a rectilinear detachable tool (13) includes a tubular sheath (1); a hollow shaft (3) rotatably mounted inside the sheath with an upstream portion (5) and a downstream portion (6) which in turn includes an upstream portion (11) partially clamped around the upstream portion (5) of the shaft and a downstream portion (12) of which the inside diameter substantially matches the outside diameter of the tool (13); a clamp (14) rigidly rotationally connected to the shaft (3) but movable along the axis thereof, which clamp is placed inside and concentric with the upstream portion (5) of the shaft; and elements for moving the clamp (14) longitudinally so that the jaws (17) thereof penetrate under the upstream portion (5) of the shaft (3) thereby gripping the tool.

15 Claims, 1 Drawing Sheet

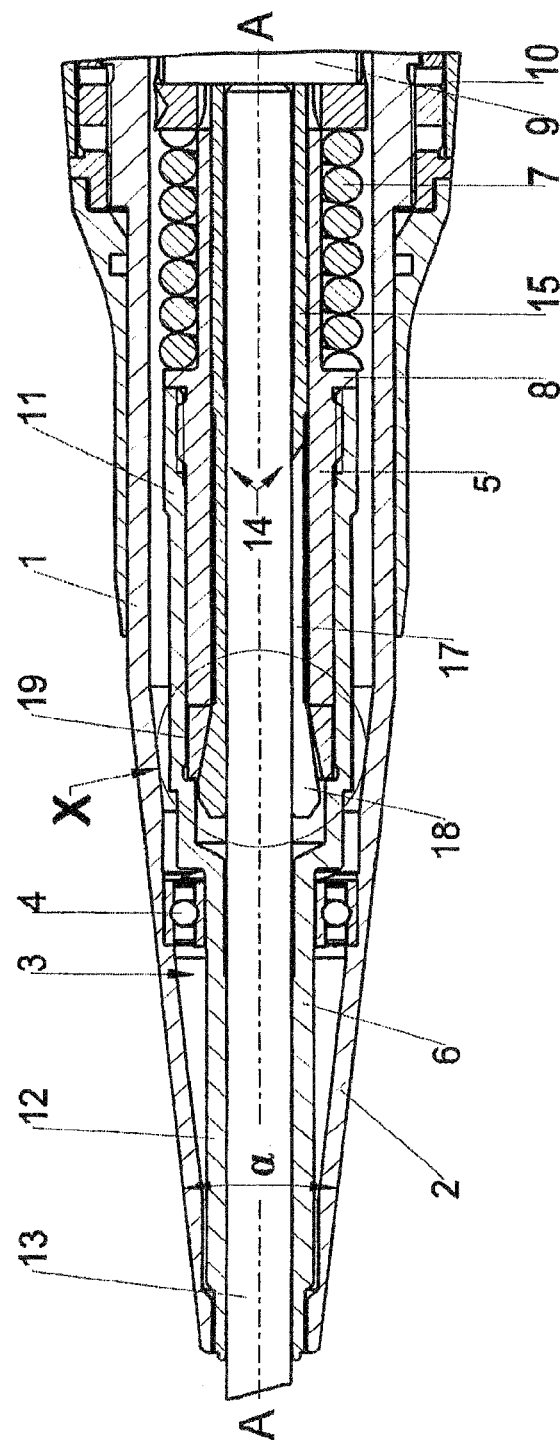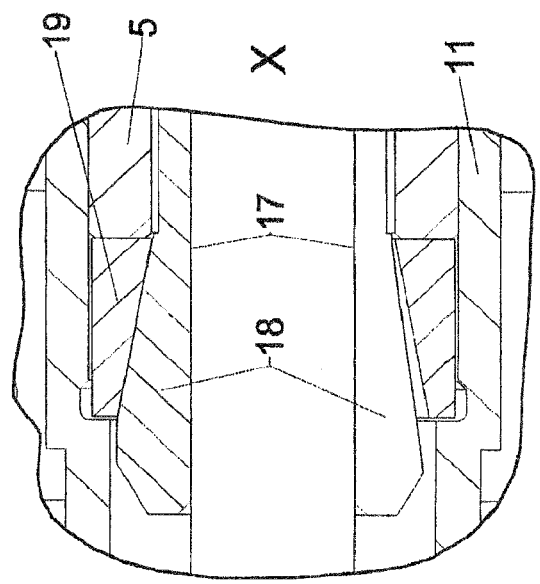
Figure 1b
Figure 1a

HAND-HELD INSTRUMENT FOR DENTAL OR SURGICAL USE

RELATED APPLICATIONS

This application is a National Stage application under 35 USC §371 of PCT/EP2007/050621, filed on Jan. 23, 2007, which claims the foreign priority of European Patent Application Serial No. 06113410.2, filed May 3, 2006.

BACKGROUND OF THE INVENTION

1) Field of the Invention

The present invention relates to the field of medical instruments. It more particularly concerns a hand-held instrument designed to rotate, at a high speed, a detachable rectilinear tool whereof the end constitutes a bur or similar member usable in dental offices or laboratories as well as in microsurgery.

2) Description of Related Art

One instrument of this type is described, for example, in document WO 2005/089666. Typically, the shank of the tool is held by a clamp arranged inside a hollow rotating shaft driven at its end by an electric motor or an air turbine and mounted by bearings in a fixed tubular sheath. Gripping and releasing of the clamp is done by turning a sleeve mounted to rotate on the shaft in one direction or the other.

In order to facilitate vision of the operation area, hand-held instruments intended for dental or microsurgical use obviously require a long, slender nose. This type of restriction unfortunately limits the possibility of ensuring good guiding of the tool at the end of the nose by means of a very small and sufficiently resistant bearing.

The shank of the tool, the diameter of which is generally only 2.35 mm, having a limited stiffness and being able to have an "out-of-round", the clamp which ensures its gripping therefore risks forcing it somewhat, which causes it to bow and the active end of the tool to oscillate. One will easily understand that this untimely shaking is very damaging to the precision of the bur's action.

The present invention aims in particular to provide an instrument wherein the noise and vibrations resulting from imperfect gripping and guiding of the shank of the tool are very greatly reduced, or even eliminated. The invention also aims to stress the ball bearing less and thereby to improve its lifespan.

SUMMARY OF THE INVENTION

More precisely, the invention concerns a hand-held instrument, for dental or surgical use, intended to rotate a rectilinear detachable tool at a high speed, the end of this tool constituting a bur or similar member. This instrument comprises:

a tubular sheath having a longitudinal axis,
 a first hollow shaft, having the same axis, mounted to rotate inside the sheath and constituted by an upstream part and a downstream part itself comprising an upstream part partially clasping the upstream part of the shaft and a downstream part whereof the internal diameter substantially corresponds to the external diameter of said tool,
 a clamp secured in rotation with the shaft but movable along said axis and placed inside the upstream part of the shaft, concentrically to it, said clamp existing, in its upstream part, in the form of a second hollow shaft whereof the internal diameter substantially corresponds to the external diameter of the tool and which, beyond this, is extended by several elastically deformable jaws intended to grip the tool, and
 means for moving said clamp longitudinally either upstream such that the jaws thereof penetrate under the upstream part of the first hollow shaft and thus ensure gripping of the tool, or downstream such that the jaws escape said upstream part and thus ensuring releasing of the tool.

BRIEF DESCRIPTION OF THE DRAWINGS

Other characteristics and advantages of the present invention will appear in the following description, done in reference to the figures:

FIG. 1a is partial longitudinal cross-section of the instrument of the present invention.

FIG. 1b is a magnified view of FIG. 1a at point X.

DETAILED DESCRIPTION OF THE INVENTION

In order to facilitate reading, the present description will use the words "upstream" and "downstream" to designate the end of the instrument from which the tool is driven in rotation (right part of the FIGURE) and its end bearing the operative tip of the tool (left part of the FIGURE), respectively. Moreover, the drawing does not show the upstream end of the instrument because it is identical to that described in the abovementioned document WO 2005/089666, to which one may refer to understand the manner in which the tool is driven.

In the drawing, 1 illustrates a cylindrical sheath, having axis AA, whereof the nose 2, downstream side, is slender to form an angle α typically between 5 and 10° ensuring that the operator has the best possible view of the operation area.

The sheath 1 essentially contains a first hollow shaft 3, having the same axis AA, whereof the upstream end is coupled to the drive shaft. This shaft is mounted to rotate in the sheath 1 thanks to a ball bearing 4 arranged in the nose 2, substantially in its middle. A second bearing (not visible in the drawing), located upstream, turns the shaft in the sheath.

The hollow shaft 3 is, indeed, made up of an upstream part 5 and a downstream part 6.

The upstream part 5 of the shaft 3 is partially surrounded by a spring 7 compressed between an edge 8 formed at its edge and a transverse bar 9, axially movable, whereof the various functions will appear below. This spring thus tends to push the bar 9 in an upstream direction.

The bar 9 can be moved in an upstream or downstream direction in longitudinal slots of the shaft 3 (not visible in the drawing) under the action of an external sleeve 10 which may be screwed or unscrewed on the upstream part of the sheath 1. In one direction of rotation of the sleeve, the bar 9 moves downstream while compressing the spring 7 whereas, in its other direction of rotation, the bar moves upstream and releases the spring.

The drawing shows that the downstream part 6 of the shaft 3 itself has an upstream part 11 and a downstream part 12, both cylindrical. The upstream part 11 clasps the upstream part 5 of the shaft 3 until it abuts on the edge 8. Its downstream part 12 has an internal diameter substantially corresponding to the external diameter of the shank 13 of the tool to be manipulated with the instrument. One will note that the bearing 4 is positioned at the upstream end of the downstream part 12.

A clamp 14, longitudinally movable, is arranged inside the upstream part 5 of the shaft 3, concentrically to it. In its upstream position, which extends substantially to the level of the rim 8 of the sheath, said clamp is in the form of a second hollow shaft 15 having an internal diameter corresponding substantially to the external diameter of the shank 13 of the tool to be manipulated. Beyond this, the shaft 15 is extended through three jaws having the same internal diameter and which are elastically deformable 17, distributed at 120° from each other, whereof the end constitutes a wedge 18 having a conical profile whereof the thickness increases in the downstream direction. The bar 9 ensures that the upstream part 5 of the shaft 3 is integral in rotation with the clamp 14.

Lastly, the upstream part 5 of the shaft 3 is extended, without being part of it, by an independent ring 19 having a conical internal profile which corresponds to the conical profile of the three wedges 18. Its constant external diameter is slightly smaller than the external diameter of the upstream part 5 of the shaft 3 so as to offer it a clearance that enables it to float between the wedges 18 and the upstream part 11 of the downstream part 6 of the shaft 3.

The drawing shows the instrument in a working position obtained by turning the sleeve 10, in an appropriate direction, around the upstream part of the sheath 1 so as to pull the bar 9 in the upstream direction. The three jaws 17 of the clamp 14 are thus also driven toward the upstream part of the clamp 14 and are inserted in the floating ring 19. With the help of the spring 7, they strongly compress the shank 13 of the tool, which thus finds itself immobilized and can be rotated by the shaft 3.

Rotation in the other direction of the sleeve 10 causes the bar 9 to return in the downstream direction, also causing the jaws 17 to slide in the downstream direction, said jaws escaping the ring 19 and, abutting on the downstream end of the upstream part 5 of the shaft (position not illustrated in the drawing), ceasing to clasp the shank 13 of the tool, which can thus be removed from the instrument.

Thus is proposed a microsurgery instrument whereof the advantages will be described below.

1. Producing the shaft 3 in an upstream part 5 which surrounds the clamp 14 and a downstream part 6 partially surrounding the upstream part 5 of the shaft, concentrically to it, and forming a barrel for the passage of the shank 13 of the tool, makes it possible to:
   perfectly align the axes of the clamp 14 and the barrel 6;
   perfectly guide the tool to the end of the nose 2 of the sheath;
   centrifuge waste to prevent it from penetrating inside the instrument.

2. Positioning the bearing 4 on the barrel 6, downstream of the clamp, offers excellent concentricity between the axis of rotation determined by the bearing and the axis of the tool.

3. The floating conical ring 19 ensuring gripping of the clamp 14 makes it possible:
   in case of slight misalignment between the axes of the barrel 6 and the clamp, because the ring is floating, to automatically align these two axes on the axis of rotation;
   in case of vibration of the tool, because the ring is floating and self-blocking, to avoid releasing of the gripping forces.

Thus, the instrument according to the invention is provided with characteristics thanks to which noise and vibrations are very greatly reduced, the effectiveness of gripping of the tool is considerably improved, guiding of the tool is perfectly ensured and the lifespan of the bearing in undeniably extended.

These advantages are particularly significant for an instrument whereof the tool, able to turn at speeds in the vicinity of 50,000 to 100,000 rotations/minute, must be able to work, without shaking, with the greatest precision.

The invention claimed is:

1. A hand-held instrument, for dental or surgical use, intended to rotate, at high speed, a detachable rectilinear tool whereof the end constitutes a bur or similar member, wherein said instrument comprises:
   a tubular sheath having a longitudinal axis,
   a first hollow shaft, having the same axis, mounted to rotate inside said tubular sheath, the first hollow shaft comprising:
   an upstream part of the first hollow shaft, and
   a downstream part of the first hollow shaft,
   the downstream part of the shaft itself comprising i) an upstream part partially clasping the upstream part of the first hollow shaft and ii) a downstream part whereof the internal diameter corresponds substantially to an external diameter of the tool,
   a clamp integral in rotation with said first hollow shaft but movable along said axis and arranged inside the upstream part of the first hollow shaft, concentrically to the first hollow shaft, said clamp existing, in its an upstream part, in the form of a second hollow shaft having an internal diameter corresponding substantially to the external diameter of the tool and which, beyond this, is extended by several elastically deformable jaws designed to grip the tool, and
   means for moving said clamp longitudinally in the upstream direction such that its jaws penetrate under the upstream part of the first hollow shaft and thus ensure gripping of the tool, and in the downstream direction such that the jaws escape said upstream part and thus ensure releasing of the tool,
   wherein the end of said jaws constitutes a wedge having a conical profile whereof the thickness increases in the downstream direction and wherein the upstream part of the first hollow shaft is extended, without being part of it, by an independent ring ensuring gripping of the clamp, said ring having a conical internal profile which corresponds to the conical profile of the wedges, a constant external diameter of said ring being slightly smaller than an external diameter of the upstream part of the first hollow shaft so as to offer it a clearance which causes it to float between the wedges and the upstream part of the downstream part of the first hollow shaft,
   wherein upstream designates an end of the instrument from which the tool is driven in rotation and downstream designates an end bearing the operative tip of the tool.

2. The instrument according to claim 1, wherein said tubular sheath has a slender nose forming an angle from 5° to 10° providing the operator with the best possible view of the operation area.

3. The instrument according to claim 2, wherein said first hollow shaft is mounted in rotation inside the tubular sheath with the help of a bearing located, in the nose of the tubular sheath, downstream of the clamp, toward the upstream end of the downstream part of the downstream part of the first hollow shaft.

4. The instrument according to claim 1, wherein said means for moving said clamp longitudinally comprise a sleeve for screwing and unscrewing on the upstream part of the tubular sheath and ensuring the longitudinal movement of the clamp.

5. The instrument according to claim 2, wherein said means for moving said clamp longitudinally comprise a sleeve for screwing and unscrewing on the upstream part of the tubular sheath and ensuring the longitudinal movement of the clamp.

6. A hand-held instrument, for dental or surgical use, intended to rotate, at high speed, a detachable rectilinear tool whereof the end constitutes a bur or similar member, the hand-held instrument comprising:
- a tubular sheath (1) having a longitudinal axis (AA) and terminating in a nose (2);
- a first hollow shaft (3), having the same longitudinal axis (AA), mounted to rotate inside said tubular sheath (1), the first hollow shaft (3) comprised of i) an upstream part (5), and ii) a downstream part (6) overlapping and abutting against the upstream part (5),
- the downstream part (6) of the first hollow shaft (3) comprising i) an upstream cylindrical part (11) partially clasping the upstream part (5) of the first hollow shaft (3) and ii) a downstream cylindrical part (12) with an internal diameter corresponding substantially to an external diameter of the tool, in use, the downstream cylindrical part (12) being immediately adjacent to the external surface of the tool;
- a clamp (14) concentrically inside the upstream part of the first hollow shaft (3) and integral in rotation with the first hollow shaft (3) and longitudinally movable along said axis (AA), the clamp comprising i) an upstream part in the form of a second hollow shaft (15) having an internal diameter corresponding substantially to the external diameter of the tool and ii) a downstream part in the form of plural elastically deformable jaws (17) adapted to grip the tool and including an end defined by a wedge (18) having a conical profile with thickness increasing in the downstream direction; and
- a bar (9) moved under action of an external sleeve (10) for moving said clamp (14) longitudinally in the upstream direction such that the jaws (17) penetrate under the upstream part (5) of the first hollow shaft (3) and thus ensure gripping of the tool, and in the downstream direction such that the jaws (17) escape said upstream part (5) of the first hollow shaft (3) and thus releasing of the tool, wherein,
- the deformable jaws including an end defined by a wedge (18) having a conical profile with thickness increasing in the downstream direction,
- the upstream part of the first hollow shaft is adjacent an independent ring ensuring gripping of the clamp,
- the independent ring having a conical internal profile corresponding to the conical profile of the wedges,
- the upstream part of the first hollow shaft being extended, without being part of the first hollow shaft, by the independent ring,
- a constant external diameter of the ring being slightly smaller than an external diameter of the upstream part of the first hollow shaft so as to float between the wedges and the upstream part of the downstream part of the first hollow shaft,
- wherein upstream designates an end of the instrument from which the tool is driven in rotation and downstream designates an end bearing the operative tip of the tool.

7. The instrument according to claim 6, wherein the nose forms an angle from 5° to 10°.

8. The instrument according to claim 7, further comprising:
- a bearing in the nose of the tubular sheath and located downstream of the clamp,
- wherein said first hollow shaft is mounted in rotation inside the tubular sheath with the help of the bearing.

9. The instrument according to claim 6, wherein said clamp is moved longitudinally by screwing and unscrewing the external sleeve on the upstream part of the tubular sheath.

10. The instrument according to claim 6, wherein the bar is a transverse bar (9) axially movable under action of the external sleeve (10), which sleeve (10) is screwed and unscrewed on the upstream part of the sheath.

11. The instrument according to claim 7, wherein, the bar is a transverse bar configured so that screwing and unscrewing the external sleeve on the upstream part of the tubular sheath and axially moves the transverse bar (9).

12. The instrument according to claim 1, wherein the downstream part of the first hollow shaft extends downstream of the end of jaws defined by wedge.

13. The instrument according to claim 6, wherein the downstream part (6) of the first hollow shaft (3) extends downstream of the downstream part of the clamp (14), including the plural elastically deformable jaws (17) the end defined by the wedge (18).

14. The instrument according to claim 1, wherein,
said upstream part of the first hollow shaft surrounds the clamp,
the downstream part of the first hollow shaft partially surrounds the upstream part of the first hollow shaft, concentrically to the upstream part of the first hollow shaft, and
the downstream part forms a barrel for the passage of the shank of the tool.

15. The instrument according to claim 6, wherein,
said upstream part (5) of the first hollow shaft (3) surrounds the clamp (14),
the downstream part (6) of the first hollow shaft (3) partially surrounds the upstream part (5) of the first hollow shaft (3), concentrically to the upstream part (5) of the first hollow shaft (3), and
the downstream part (6) forms a barrel for the passage of the shank (13) of the tool.

* * * * *